US012806005B2

(12) United States Patent
Detry et al.

(10) Patent No.: US 12,806,005 B2
(45) Date of Patent: Nov. 24, 2026

(54) PACKAGE FOR RETAINING AND DISPENSING A DELIVERY SHAFT ASSEMBLY FOR DELIVERY OF AN IMPLANT

(71) Applicant: ISTAR MEDICAL, Wavre (BE)

(72) Inventors: Benoit Detry, Alleur (BE); Isabelle Bouhy, Tamines (BE); Stefan Uhrlandt, Hamburg (DE); Adrien Bernard Girod, Biel (CH)

(73) Assignee: iSTAR Medical SA, Wavre (BE)

( * ) Notice: Subject to any disclaimer, the term of this patent is extended or adjusted under 35 U.S.C. 154(b) by 962 days.

(21) Appl. No.: 17/802,635

(22) PCT Filed: Feb. 26, 2021

(86) PCT No.: PCT/EP2021/054858
§ 371 (c)(1),
(2) Date: Aug. 26, 2022

(87) PCT Pub. No.: WO2021/170812
PCT Pub. Date: Sep. 2, 2021

(65) Prior Publication Data

US 2023/0101775 A1 Mar. 30, 2023

(30) Foreign Application Priority Data

Feb. 27, 2020 (EP) .................................... 20159797

(51) Int. Cl.
*A61F 2/16* (2006.01)
*A61F 2/00* (2006.01)
(Continued)

(52) U.S. Cl.
CPC .......... *A61F 2/1691* (2013.01); *A61F 2/0095* (2013.01); *A61F 2/148* (2013.01); *A61F 9/0017* (2013.01); *A61J 1/2096* (2013.01)

(58) Field of Classification Search
CPC .... A61F 9/0017; A61F 2/1691; A61F 2/0095; A61F 2/1678
See application file for complete search history.

(56) References Cited

U.S. PATENT DOCUMENTS 5,817,075 A * 10/1998 Giungo .............. A61B 17/3468 606/166
6,387,101 B1 * 5/2002 Butts ..................... A61F 2/1664 606/107
(Continued)

FOREIGN PATENT DOCUMENTS

EP 2111820 A1 * 10/2009 ........... A61F 2/1691
NL 2010675 C2 10/2014
(Continued)

OTHER PUBLICATIONS

PCT International Search Report and Written Opinion; Application No. PCT/EP2021/054858, filing date of Feb. 26, 2021 Istar Medical SA, date of mailing Jun. 11, 2021, 10 pages.

*Primary Examiner* — Sarah Al Hashimi
*Assistant Examiner* — Arjuna P Chatrathi
(74) *Attorney, Agent, or Firm* — Patent Law Works LLP

(57) ABSTRACT

Provided is a package (100) for holding and dispensing a delivery shaft assembly (200) for delivery of an implant (230), the package (100) comprising a vial (400) and an insert (300) mounted within a vial holding space (410), wherein the insert (300) comprises:

- a force receiving body (308) configured to support an adapter (210) of a delivery shaft assembly (200) during coupling to the inserter tool (500),
- a delivery shaft retaining mechanism (310) configured to releasably retain the delivery shaft, wherein an application of force by an inserter tool (500) during coupling to the adapter (210) actuates the delivery shaft retaining mechanism (310) to release the retained (Continued)

delivery shaft (220) for withdrawal of the delivery shaft assembly (200) from the insert (300) and vial (400).

11 Claims, 5 Drawing Sheets

(51) Int. Cl.

| | |
|---|---|
| ***A61F 2/14*** | (2006.01) |
| ***A61F 9/00*** | (2006.01) |
| ***A61J 1/20*** | (2006.01) |

(56) References Cited

U.S. PATENT DOCUMENTS

| | | | | |
|---|---|---|---|---|
| 10,869,754 | B2 | 12/2020 | Pagnoulle et al. | |
| 2003/0045930 | A1* | 3/2003 | Nguyen | A61F 2/16 606/107 |
| 2007/0000801 | A1* | 1/2007 | Mauran | A61F 2/167 206/438 |
| 2007/0060925 | A1* | 3/2007 | Pynson | A61F 2/1664 606/107 |
| 2007/0250068 | A1* | 10/2007 | Vincent-Aubry | A61F 2/1678 606/107 |
| 2008/0114373 | A1* | 5/2008 | Rathert | A61F 2/1691 606/107 |
| 2009/0182421 | A1 | 7/2009 | Silvestrini et al. | |
| 2012/0311839 | A1* | 12/2012 | Limaye | A61M 5/002 29/700 |
| 2013/0023892 | A1* | 1/2013 | Schneider | A61F 2/142 606/107 |
| 2014/0163448 | A1 | 6/2014 | Lind et al. | |
| 2017/0079839 | A1* | 3/2017 | Schaller | A61F 9/0017 |
| 2017/0165108 | A1* | 6/2017 | Bianchi | A61F 9/007 |
| 2018/0368886 | A1* | 12/2018 | Navratil | A61F 9/0017 |
| 2019/0038462 | A1 | 2/2019 | Vandiest | |
| 2019/0105151 | A1* | 4/2019 | Tseng | A61F 2/1691 |
| 2023/0101775 | A1 | 3/2023 | Detry et al. | |

FOREIGN PATENT DOCUMENTS

| | | | |
|---|---|---|---|
| WO | 2005110289 | A1 | 11/2005 |
| WO | 2011006078 | A1 | 1/2011 |
| WO | 2016011191 | A1 | 1/2016 |
| WO | 2017108498 | A1 | 6/2017 |
| WO | 2017182508 | A1 | 10/2017 |

* cited by examiner

PACKAGE FOR RETAINING AND DISPENSING A DELIVERY SHAFT ASSEMBLY FOR DELIVERY OF AN IMPLANT

CROSS REFERENCE TO RELATED APPLICATIONS

This application is a national phase entry under 35 U.S.C. § 371 of International Patent Application PCT/EP2021/054858, filed Feb. 26, 2021, designating the United States of America and published in English as International Patent Publication WO 2021/170812 on Sep. 2, 2021, which claims the benefit under Article 8 of the Patent Cooperation Treaty to European Patent Application Serial No. 20159797.8, filed Feb. 27, 2020, the entireties of each of which are hereby incorporated by reference.

FIELD OF THE INVENTION

Provided herein is a package for retaining and dispensing a delivery shaft assembly for delivery of an implant for implantation in a subject.

BACKGROUND TO THE INVENTION

Implants are often used to treat conditions where medicinal treatment has become ineffective or is not available. Techniques for placement of an implant typically rely on an inserter tool that temporarily holds the implants and provides an elongated reach for placement at the implantation site and a mechanism for ejection from the inserter. Implants can be very small, for instance, implants for the treatment of glaucoma typically have a length of 5 mm and a width of 1 mm. An example of an implant and inserter too for treatment of glaucoma is disclosed, for instance, in WO 2017/108498.

A problem in the art is how to store the implant prior to use so that it is in an optimum condition. A small implant can be difficult to load into an inserter just prior to use. Some implants need to be maintained under liquid storage without damage or without being exposed to air pockets.

SUMMARY

Described herein is a package (100) for holding and dispensing a delivery shaft assembly (200) for delivery of an implant (230), wherein the delivery shaft assembly (200) comprises a delivery shaft (220) having a lumen (222) holding the implant (230), and an adapter (210) configured for coupling to an inserter tool (500), the inserter tool (500) is provided with a discharge shaft (510) configured to be received by the delivery shaft assembly lumen (222), and with an adapter coupling (520) configured to couple with the adapter (210), wherein the delivery shaft (220) and/or of the discharge shaft (510) is moveable such that the implant (230) is released from the lumen, the package (100) comprising:

a vial (400) and an insert (300) mounted within a vial holding space (410), wherein the insert (300) comprises:

a force receiving body (308) configured to support the adapter (210) during coupling to the inserter tool (500), a delivery shaft retaining mechanism (310) configured to releasably retain the delivery shaft, wherein an application of force by the inserter tool (500) during coupling to the adapter (210) actuates the delivery shaft retaining mechanism (310) to release the retained delivery shaft (220) for withdrawal of the delivery shaft assembly (200) from the insert (300) and vial (400).

The delivery shaft retaining mechanism (310) may comprise a 1st body (312) and 2nd body (314) configured to co-operate to clamp at least a part of the delivery shaft (220).

The 1st body (312) may be disposed in fixed relation to the force-receiving body (308), and the 2nd body (314) is configured to at least partly move upon actuation of the delivery shaft retaining mechanism (310) away from the 1st body (312) thereby releasing the retained delivery shaft (220).

The delivery shaft retaining mechanism (310) may further comprise an actuating pin (316) and a movement guide (318) wherein an application of force by the inserter tool during coupling advances the pin (316) and movement guide (318) from a retain position to a release position, wherein the movement guide (318), slidably coupled to the 2nd body (314), effects movement of the 2nd body (314) from a retain position to a release position.

The movement guide (318) may comprise at least 1 guiding slot (320) having at least a partly cammed path, the 2nd body (314) may comprise at least one protrusion (322) engaged in the guiding slot (320), movement of the movement guide (318) from the retain to release position may effect sliding of the guiding slot (320) and movement of the at least one protrusion (322) along the cammed path thereby separating at least a part of the 2nd body (314) from the 1st body (312).

The 1st body (312) and the 2nd body (314) may be connected by a hinge, preferably by a living hinge. The vial holding space (410) may be configured for retention of a liquid. The vial (400) may have an opening (412), closable by a cap or removable seal.

The 1st body (312) may be provided with a keeper (324), configured to limit movement of the implant (230) in the delivery shaft (220) lumen (222) in the distal end (40) direction.

The keeper may comprise a projection configured to at least partly engage with the delivery shaft (220) lumen (222).

The 1st body (312) and 2nd body (314) co-operate to clamp at least a part of the delivery shaft in a clamping region such that the delivery shaft lumen (222) in the clamping region (**312*a*, 314*a*) is at least partly narrowed, thereby limiting movement of the implant (230) in a proximal (20**) direction.

The insert (300) may further comprise one or more fluid displacement bodies (340) configured to displace (aqueous) solution from vial holding space (410) during coupling of the insert (300) into the vial holding space (410).

The insert (300) may further comprises an overflow outlet (342) configured for passage of the displaced solution from the vial. The package (100) may further comprise the delivery shaft assembly (200) as defined herein.

FIGURE LEGENDS

FIG. 1 view of a delivery shaft assembly as described herein

FIG. 2 view of a package as described herein.

DETAILED DESCRIPTION OF INVENTION

Figure 1:
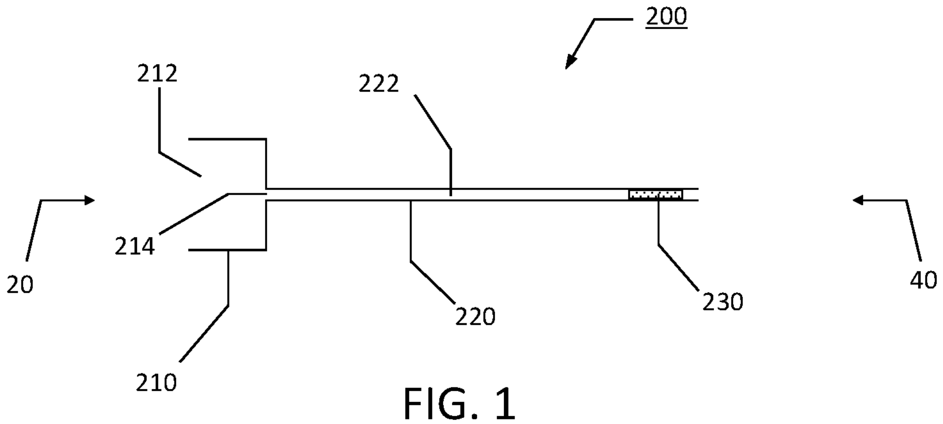

Before the present system and method of the invention are described, it is to be understood that this invention is not limited to particular systems and methods or combinations described, since such systems and methods and combinations may, of course, vary. It is also to be understood that the terminology used herein is not intended to be limiting, since the scope of the present invention will be limited only by the appended claims.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. It will be appreciated that the terms "comprising", "comprises" and "comprised of" as used herein comprise the terms "consisting of", "consists" and "consists of".

The recitation of numerical ranges by endpoints includes all numbers and fractions subsumed within the respective ranges, as well as the recited endpoints.

The term "about" or "approximately" as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" or "approximately" refers is itself also specifically, and preferably, disclosed.

Whereas the terms "one or more" or "at least one", such as one or more or at least one member(s) of a group of members, is clear per se, by means of further exemplification, the term encompasses inter alia a reference to any one of said members, or to any two or more of said members, such as, e.g., any ≥3, ≥4, ≥5, ≥6 or ≥7 etc. of said members, and up to all said members.

All references cited in the present specification are hereby incorporated by reference in their entirety. In particular, the teachings of all references herein specifically referred to are incorporated by reference.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the appended claims, any of the claimed embodiments can be used in any combination.

In the present description of the invention, reference is made to the accompanying drawings that form a part hereof, and in which are shown by way of illustration only of specific embodiments in which the invention may be practiced. Parenthesized or emboldened reference numerals affixed to respective elements merely exemplify the elements by way of example, with which it is not intended to limit the respective elements. It is to be understood that other embodiments may be utilised and structural or logical changes may be made without departing from the scope of the present invention. The following detailed description, therefore, is not to be taken in a limiting sense, and the scope of the present invention is defined by the appended claims.

The terms "distal" or "distal to" and "proximal" or "proximal to" are used throughout the specification, and are terms generally understood in the field to mean towards (proximal) or away (distal) from the user's (practitioners) side of an apparatus. Thus, "proximal" or "proximal to" means towards the user's side and, therefore, away from the subject's (patient's) side. Conversely, "distal" or "distal to" means towards the subject's side and, therefore, away from the users side. The term "subject" refers to the human or animal receiving the implant. The term "user" refers to the person performing the implantation (e.g. surgeon, specialist, practitioner).

Figure 2:
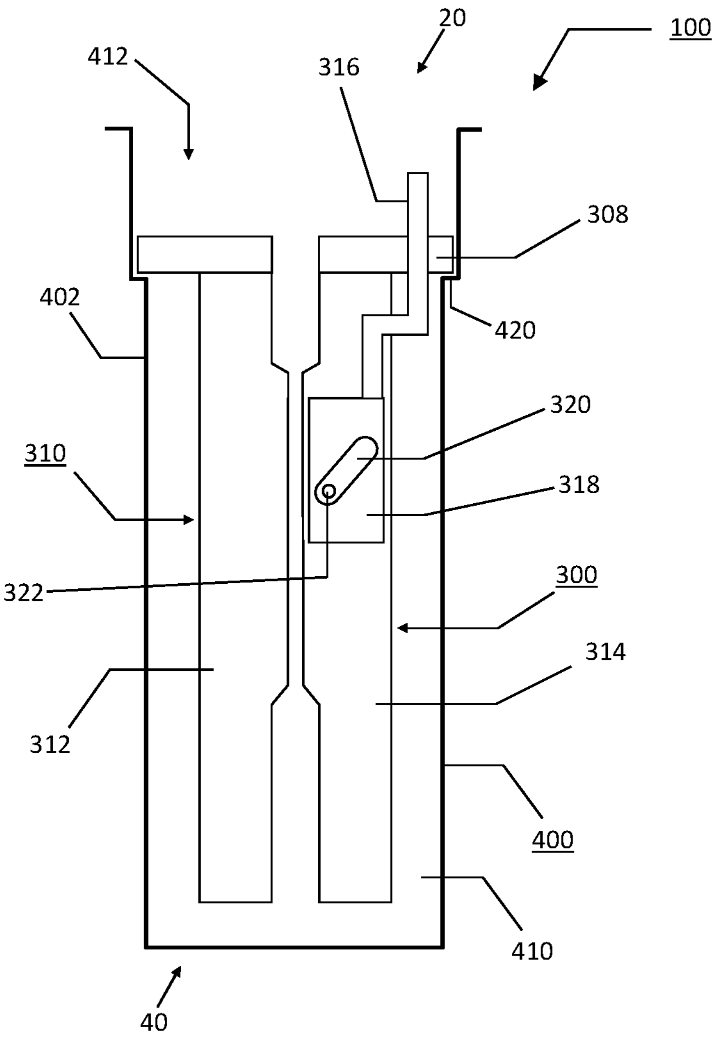

Provided herein is a package (100) for holding and dispensing a delivery shaft assembly (200) for delivery of an implant (230) as exemplified for instance in FIGS. 1 and 2. The package (100) comprises a vial (400) and an insert (300) mounted within a vial holding space (410). The vial holding space (410) is typically provided with a liquid to maintain the implant (230) in a state e.g. hydrated for implantation. The insert (300) comprises a force receiving body (308) configured to support an adapter (210) of delivery shaft assembly (200) during coupling to an inserter tool (500). The insert (300) further comprises a shaft retaining mechanism (310) configured to releasably retain a delivery shaft (220) of the delivery shaft assembly (200). The shaft retaining mechanism (310) is configured such that an application of force by the inserter tool (500) during coupling to the adapter (210) actuates the shaft retaining mechanism (310) to release the retained delivery shaft (220) for withdrawal of the delivery shaft assembly (200) from the insert (300) and vial (400).

Advantageously, the package (100) stabilises the position of the delivery shaft assembly (200) within the vial (400) during transport and storage, preventing unintentional loss of implant from the delivery shaft by transport and handling agitation. By linking a release or retain state of shaft retaining mechanism (310) to an application of force by the inserter tool (500), the delivery shaft assembly (200) is retained in the vial holding space (410) and liquid up until the moment of use, and is released from the insert (300) at the same time as inserter tool couples to it. The package (100) may or may not include the delivery shaft assembly (200). The package (100) may or may not include the inserter tool (500).

The delivery shaft assembly (200) comprises an adapter (210) and a delivery shaft (220). The delivery shaft (220) is provided with a lumen (222) holding the implant (230), and an adapter (210) configured for coupling to the inserter tool (500). The implant (230) is disposed at or towards a distal end (40) of the delivery shaft (220). The adapter (210) is disposed at a proximal end (20) of the delivery shaft (220). The adapter (210) has a body provided with a receiving space (212) fora part of the inserter tool (500) and an aperture (214) connecting the receiving space (212) to a lumen (222) of delivery shaft (220). The lumen (222) is configured for the passage of a discharge shaft (510) of the inserter tool (500) therethrough. The implant (230) may be ejected from the delivery shaft (220) by actuation of the inserter tool (500), thereby delivering the implant (230) to the target. An exemplary delivery shaft assembly (200) is disclosed in WO 2017/108498, which is incorporated herein by reference.

The inserter tool (500) is provided with a discharge shaft (510) configured to be received by the delivery shaft assembly lumen (220). The discharge shaft (510) may be configured abut the implant (230). Movement of the delivery shaft (220) and/or of the discharge shaft (510) causes release of the implant (230) from the lumen (222)

Advancement of the discharge shaft (510) in a distal (40) direction may apply force to the implant (230), causing it to be ejected from the shaft assembly lumen (220). Alternatively or additionally, withdrawal of the delivery shaft (220) relative to a fixed discharge shaft (510) causes the implant (230) to be ejected from the shaft assembly lumen (220).

The inserter tool (500) is provided with an adapter coupling (520) configured to couple with the adapter (210). The coupling between the adapter coupling (520) and adapter (210) may be releasable or non-releasable. A non-releasable coupling may be achieved, for instance, by providing a compliant member on one of the adapter coupling (520) or adapter (210) and a reciprocating stop member on the other, wherein the compliant member slides across the stop member in one direction during couple the parts (520, 210) and the compliant member engages with the stop member in the other sliding direction to prevent release of the parts (520, 210). The mechanism is similar to the one-directional movement of a ratchet mechanism.

Where the implant is ejected by withdrawal of the delivery shaft (220) relative to the fixed discharge shaft (510), the adapter coupling (520) may be slidable relative to the fixed discharge shaft (510). The slidable adapter coupling (520) has a primed and deployed position. In the primed position, the slidable adapter coupling (520) places the adapter (210) and delivery shaft lumen (222) in a distal-most position. The fixed discharge shaft (510) may abut the implant (230) and the delivery shaft lumen (222) may cover the implant (230). In the deployed position, the slidable adapter coupling (520) places the adapter (210) and delivery shaft lumen (222) in a proximal-most position. The discharge shaft (510) abuts the implant (230) and the delivery shaft lumen (222) is withdrawn in a proximal (20) direction and the implant (230) is released. Where the implant is ejected by advancement of the discharge shaft (510), the discharge shaft (510) slidable relative to a fixed adapter coupling (520) applied an ejection force in a distal direction upon the implant (230) causing it to be ejected from the lumen (222).

Figure 5:
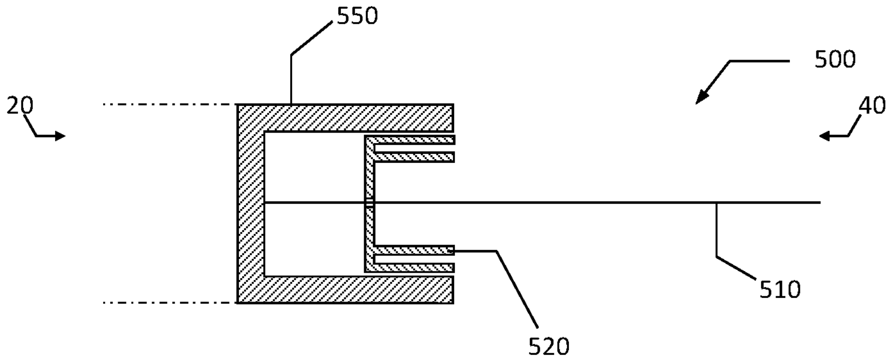
FIG. 5 shows a part of an inserter tool as described herein.

An example of a part of an inserter tool (500) is provided in FIG. 5, showing an inserter housing or chassis (550) (fixed), and a slidable adapter coupling (520) configured to engage with the adapter (210) of the delivery shaft assembly (200). A discharge shaft (510) is disposed in fixed relation to the housing (550). When the adapter (210) is engaged in the adapter coupling (520), the delivery shaft assembly (200) can be lifted from the package (100) while the movement guide (318) is in the release position. In this example, the adapter coupling (520) is slidable relative to the housing (550) and is shown in a primed position; it is appreciated that the other configurations of the inserter tool (500) exist, for instance, in which the adapter coupling (520) is disposed in fixed relation to an inserter tool housing and the discharge shaft (510) is slidable.

Figure 7:
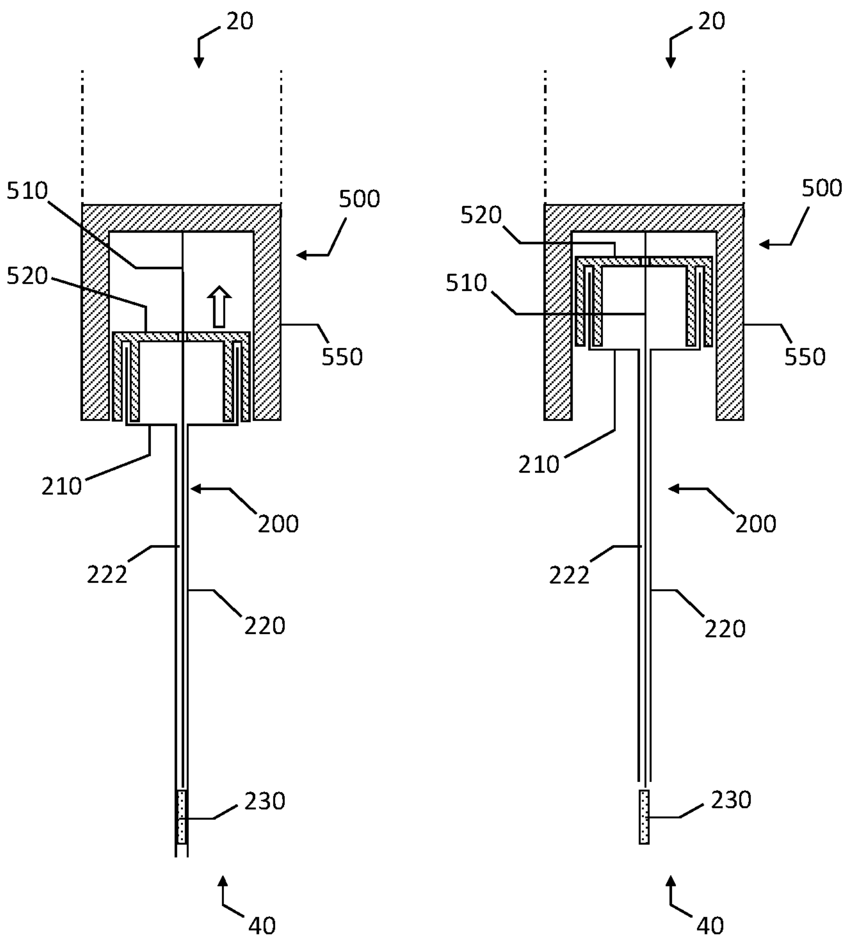
FIGS. 7A and 7B show the inserter tool in a primed (FIG. 7A) and deployed (FIG. 7B) configuration.

FIGS. 7A and 7B illustrates a part of an inserter tool (500) showing an inserter housing or chassis (550) (fixed), and a slidable adapter coupling (520) coupled with the adapter (210) of the delivery shaft assembly (200). In FIG. 7A, the inserter tool (500) is shown in the primed position; the adapter coupling (520) is in a distal (40) position. In the primed position, the implant (230) is retained in the delivery shaft lumen (222). In FIG. 7B, the inserter tool (500) is shown in the deployed position; the adapter coupling (520) is withdrawn to a proximal (20) position. In the deployed position, the delivery shaft is withdrawn, thereby releasing the implant (230) from the delivery shaft lumen (222).

An exemplary inserter tool (500) is disclosed in WO 2017/108498, which is incorporated herein by reference.

The shaft retaining mechanism (310) may have a retain state (in which the delivery shaft (222) and hence delivery shaft assembly (200) are held fast by the shaft retaining mechanism (310)) and a release state (in which the delivery shaft (222) and hence delivery shaft assembly (200) are free of the insert (300)). Movement from the retain state to the release state is actuated by force of the inserter tool (500) during coupling to the adapter (210). An exemplary shaft retaining mechanism (310) is shown in FIGS. 2, 3A to 3C, 4.

The shaft retaining mechanism (310) may comprise a 1st body (312) and 2nd body (314) configured to co-operate (in the retain state) to clamp at least a part of the delivery shaft (222). The delivery shaft (220) may be clamped in fixed relation to the force receiving body.

Figure 4:
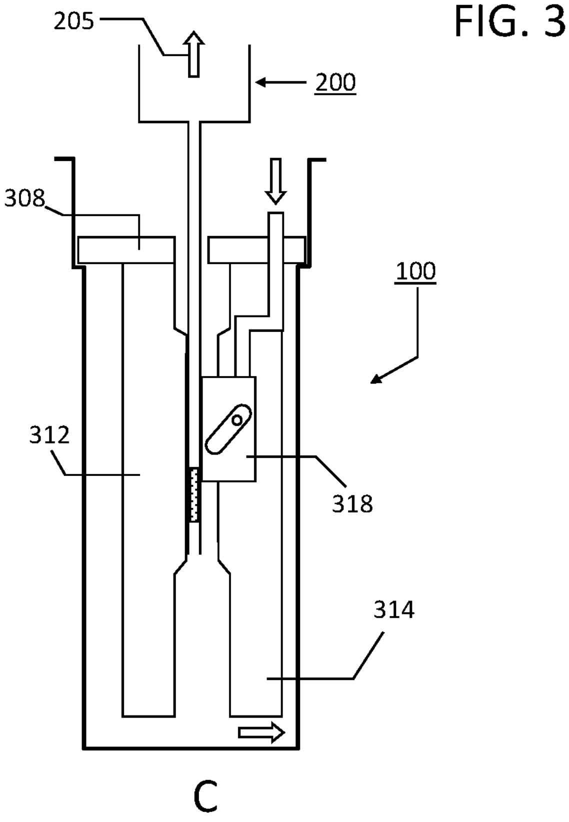
FIG. 4 shows a package as described herein, emphasising clamping parts of the $1^{st}$ body and $2^{nd}$ body that narrow the delivery shaft, and showing the keeper.
Figure 4:
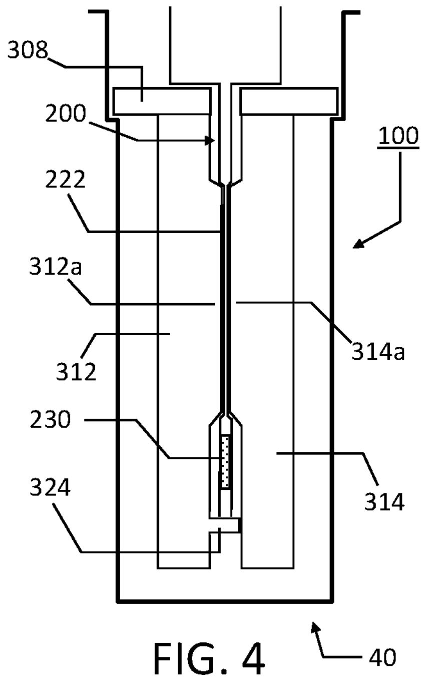

The 1st body (312) and 2nd body (314) may co-operate in the retain state to clamp at least a part of the delivery shaft in a clamping region (312*a*, 314*a*) such that the delivery shaft lumen (222) in the clamping region is at least partly narrowed, thereby limiting movement of the implant (230) in a proximal (20) direction. An exemplary clamping region (312*a*, 314*a*) narrowing the delivery shaft lumen (222) is shown in FIG. 4.

The 1st body (312) may be disposed in fixed (non-moveable) relation to the force-receiving body (308). The 2nd body (314) may be configured to at least partly move upon actuation of the shaft retaining mechanism (310) away from the 1st body (312) thereby releasing the retained delivery shaft (220).

The $1^{st}$ body (312) and $2^{nd}$ body (314) may be longitudinal. The $1^{st}$ body (312) and $2^{nd}$ body (314) may be longitudinal in a proximal-distal direction. The 1st body (312) and the 2nd body (314) may be connected by a hinge (e.g. living hinge).

The shaft retaining mechanism (310) may further comprising an actuating pin (316) and a movement guide (318). The actuating pin (316) may be attached in fixed relation to the movement guide (318). An application of force by the inserter tool (500) during coupling advances the pin (316) and movement guide (318) from a retain position to a release position. The movement guide (318), slidably coupled to the 2nd body (314), effects movement of the 2nd body (314) from a retain position to a release position.

The movement guide (318) comprises at least 1, or 2 or more (preferably 2) guiding slots (320) having at least a partly cammed path. The cammed path is a linear cam that translates a linear movement in a $1^{st}$ direction (e.g. proximal-distal) to a linear movement in a $2^{nd}$ direction (e.g. perpendicular to the $1^{st}$ direction).

The 2nd body (314) may comprise a protrusion (322) engaged in a guiding slot (320). There may be one protrusion (322) per guiding slot (320). The protrusion (322) may be fixed relation to the 2nd body. The protrusion (322) may be a follower for the cammed path.

Movement of the movement guide (318) from the retain to release position effects sliding (in a $1^{st}$ direction) of the guiding slot (320) and movement (in a $2^{nd}$ direction) of the protrusion (322) along the cammed path thereby separating at least a part of the 2nd body (314) from the 1st body (312).

Figure 3:
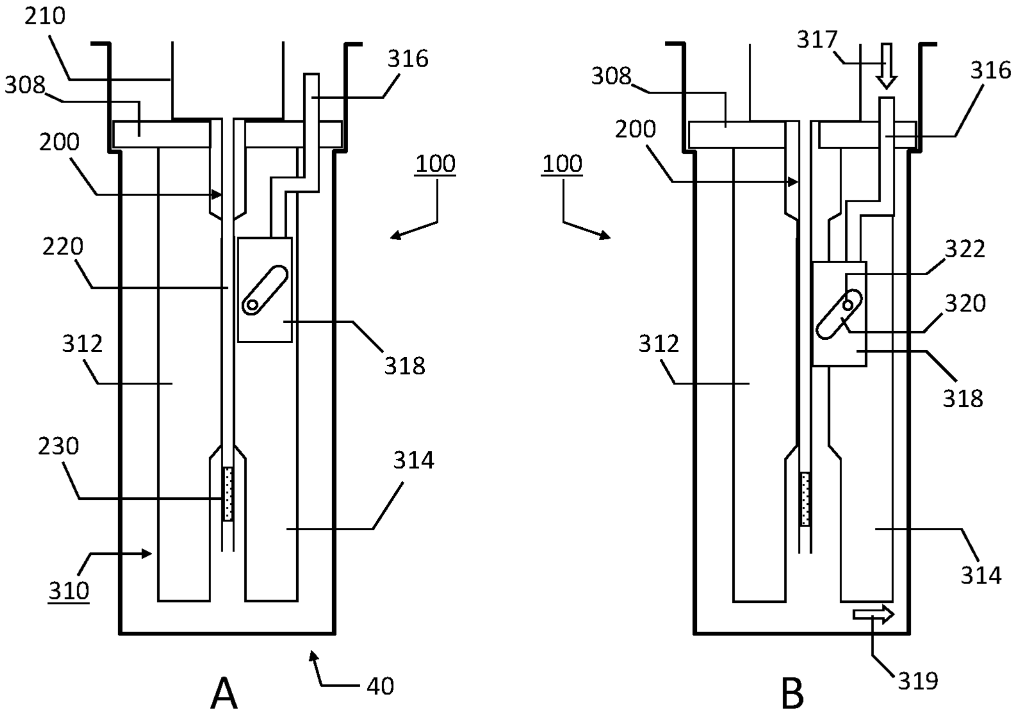
FIGS. 3A-3C are a sequence of views showing actuation of the retaining shaft mechanism and release of the delivery shaft assembly.

FIGS. 3A-3C show a package (100) as described herein provided with a delivery shaft assembly (200), illustrating steps of activating the shaft retaining mechanism (310) to move it from a retain state (FIG. 3A) to a release state (FIGS. 3B and 3C). In FIG. 3A, the shaft retaining mechanism (310) in the retain state clamps the delivery shaft (220) between the 1st body (312) and 2nd body (314). In FIG. 3B, downward force (proximal-distal) (317) applied to the actuating pin (316) displaces the movement guide (318) in a downward direction. The protrusion (322) or follower engaged in the guiding slot (320) is displaced laterally (319), causing movement of the $2^{nd}$ body in a lateral direction, thereby moving the shaft retaining mechanism (310) to the release state. The delivery shaft assembly (200) is released, and can be withdrawn (205) (FIG. 3C) from the insert (300) and hence from the package (100).

Figure 6:
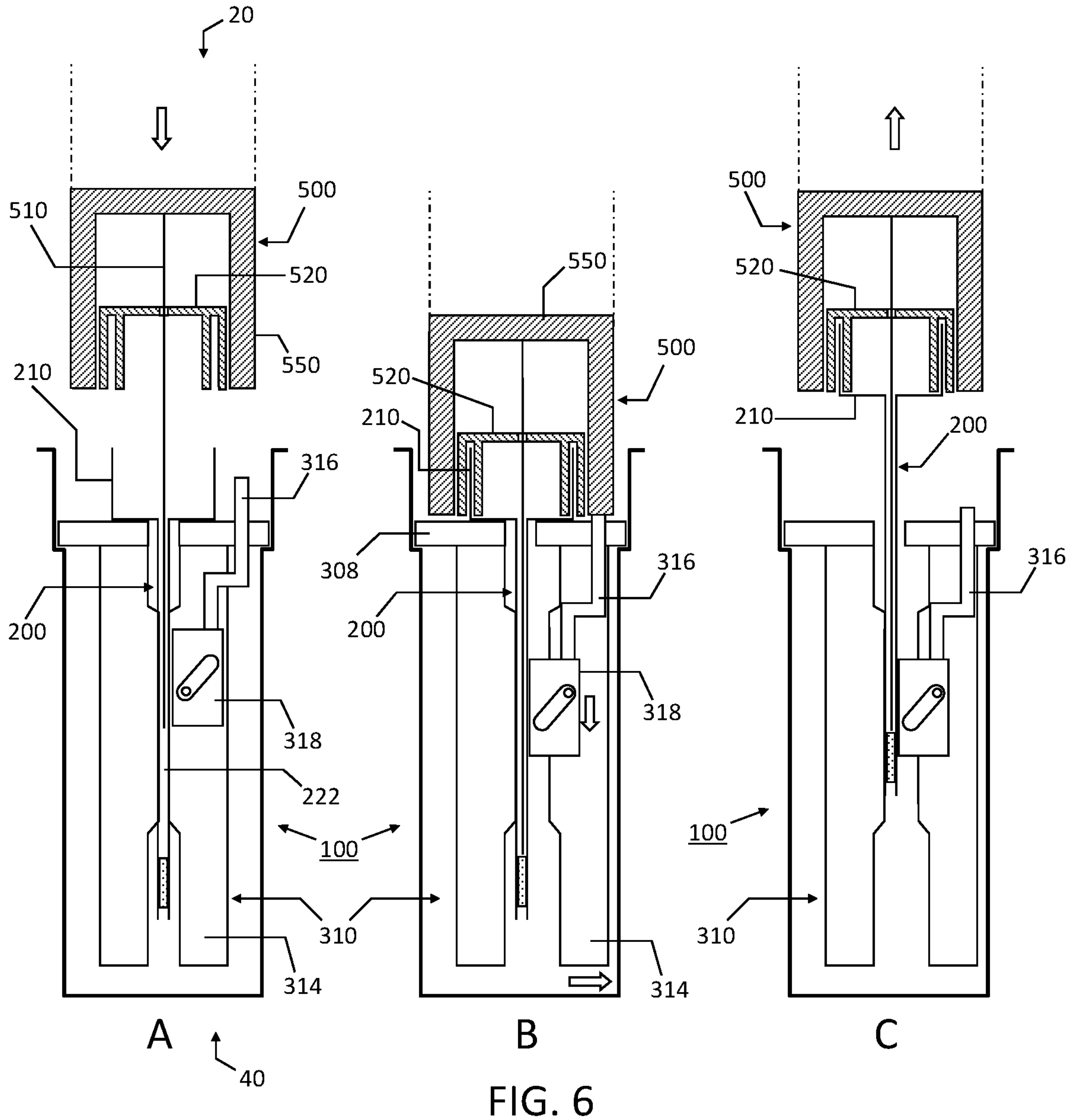
FIGS. 6A-6C show a sequence of views in which the inserter tool couples with a delivery shaft assembly, and the retaining shaft mechanism is actuated to release of the delivery shaft assembly.

FIGS. 6A-6C show a package (100) as described herein provided with a delivery shaft assembly (200), illustrating steps of activating the shaft retaining mechanism (310) to move it from a retain state (FIG. 6A) to a release state (FIG. 6B), coupling of the adapter coupling (520) with the adapter (210) (FIG. 6B), and withdrawal of the delivery shaft assembly (200) from the package (100) (FIG. 6C). In FIG. 6A, the adapter coupling (520) is in a primed position, and the discharge shaft (510) is inserted into the delivery shaft lumen (222). In FIG. 6B, the inserter housing (550) pushes downwards against the actuating pin (316) thereby actuating the movement guide (318) causing movement of the $2^{nd}$ body (314) to a release position. In FIG. 6B, the inserter adapter coupling (520) in the primed position couples with the deliver shaft assembly adapter (210). The adapter (210) is supported at its distal end by the force receiving surface (308) while the inserter adapter coupling (520) presses downwards (in a distal direction) on the adapter (210) to effect coupling. In FIG. 6C, with inserter adapter coupling (520) still in the primed position and the shaft retaining mechanism (310) in a release position, the delivery shaft assembly (200) can be withdrawn from the package (100) coupled to the inserter tool (500).

The 1st body (312) or second body (314), preferably the $1^{st}$ body (312) may be provided with a keeper (324). The keeper may be disposed in fixed (non-moveable) relation to the $1^{st}$ body (312) or $2^{nd}$ body (314) respectively. The keeper (324) is configured to co-operate with a distal tip of the delivery shaft (220) to limit movement of the implant (230) in the distal end (40) direction. The keeper (324) may comprises a projection (e.g. conical) configured to at least partly engage with the delivery shaft (220) lumen (222). The keeper (324) may be a solid body extending laterally (perpendicular to a proximal-distal direction). FIG. 4 illustrates a keeper (324) fixed to a distal end (40) of the $1^{st}$ body (312). The keeper (324) covers a distal end (40) of the delivery shaft lumen (222), and retains the implant (230) by blocking a distal (40) passage of the implant (230). The keeper (324) limits movement of the implant in a distal direction (40).

Figure 8:
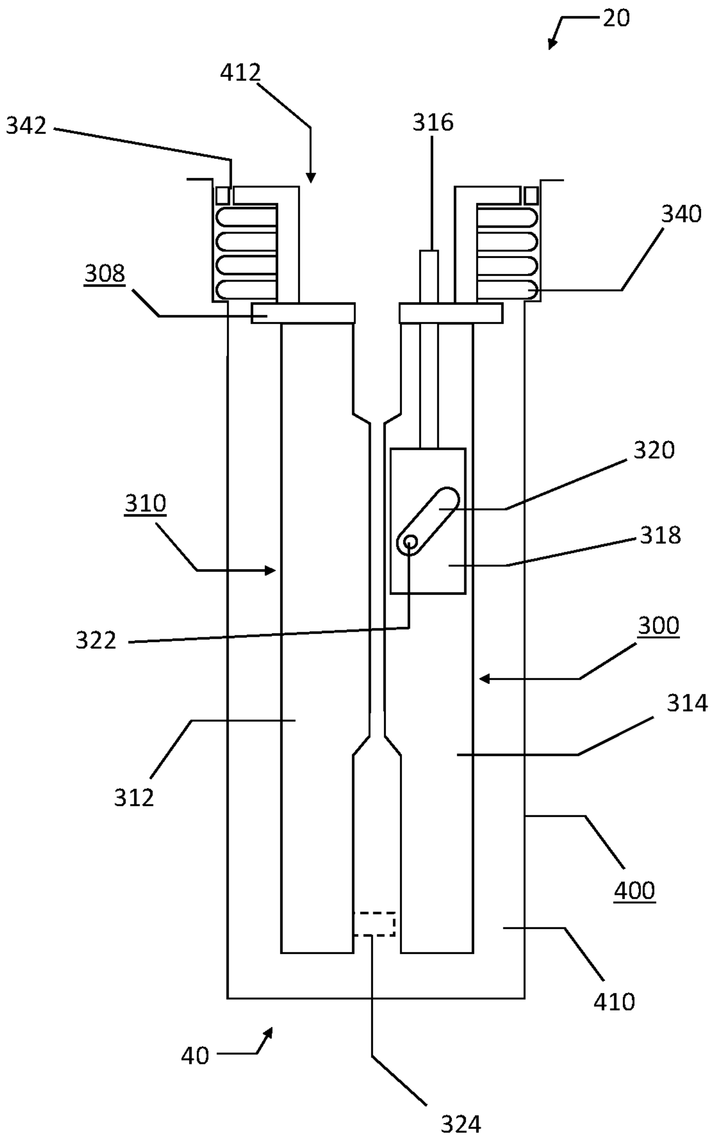
FIG. 8 depicts a package as described herein further provided with a plurality of liquid displacement bodies.

The insert (300) may further comprise one or more liquid displacement bodies (340). A fluid displacement body (340) is configured to displace liquid from vial holding space (410) during placement of the insert (300) during assembly of the package (100). This allows the vial holding space (410) to be filled with a minimum of air bubbles. A liquid displacement body (340) may have a ring-like appearance. The insert (300) may further comprise an overflow outlet (342) configured for passage of the displaced liquid from the vial. The overflow outlet (342) may extend in a proximal direction as a channel into the one or more liquid displacement bodies (340). FIG. 8 shows a plurality of liquid displacement bodies (340) disposed at a proximal (20) end of the insert (300), and an overflow outlet (342) through which excess liquid is expelled from the holding space (410).

The vial (400) may be formed from a vial body (402) that defines the vial holding space (410). The vial holding space (410) is configured for retention of a liquid e.g. aqueous solution, organic solvent. The vial (400) has an opening (412) at the proximal end (20) configured to receive a distal part of the inserter tool (500). The opening (412) may be closed by a cap or removable seal. The vial (400) may be disposed with one or more support members (420) configured to support the insert (300). The support member (420) is configured limit movement of the insert (300) in a distal (40) direction. In particular, when force is applied by the inserter tool (500) to the force receiving surface (308), the support member (420) prevents movement of and damage to the insert (300). The support member (420) may be provided as a ridge on the vial body (402) that engages with the force receiving body (308). An exemplary vial is shown in detail in FIG. 2.

The implant (230) may be any placeable in a subject (animal, human) using an inserter tool. In particular, the implant (230) may be an implant for treatment of glaucoma. In particular, the implant (230) may be an intraocular shunt. The implant (230) may be for implantation between the sclera and the choroid, i.e. in the suprachoroidal space. The implant (230) be an implant as described in WO 2017/108498. In particular, the implant may be as described on page 13, lines 1 to page 14, line 5, and/or on page 21, line 25 to page 22 line 21 of WO 2017/108498 which is incorporated herein by reference.

The inserter tool (500) may be an implantation device as described in WO 2017/108498. The delivery shaft assembly (200) may comprise a one-touch fitting connection element or adaptor (210) as described in WO 2017/108498. For example, WO 2017/108498 describes an implantation device (500) and delivery shaft assembly (200) on pages 26 to page 33 which is incorporated herein by reference.

The invention claimed is:

1. A package (100) for holding and dispensing a delivery shaft assembly (200) for delivery of an implant (230), wherein the delivery shaft assembly (200) comprises a delivery shaft (220) having a lumen (222) holding the implant (230), and an adapter (210) configured for coupling to an inserter tool (500), and the inserter tool (500) is provided with a discharge shaft (510) configured to be received by the delivery shaft assembly lumen (222), and with an adapter coupling (520) configured to couple with the adapter (210), wherein the delivery shaft (220) and/or of the discharge shaft (510) is moveable such that the implant (230) is released from the lumen, the package (100) comprising:

a vial (400) and an insert (300) mounted within a vial holding space (410), wherein the insert (300) comprises:

a force receiving body (308) configured to support the adapter (210) during coupling to the inserter tool (500), and a delivery shaft retaining mechanism (310) configured to releasably retain the delivery shaft, wherein an application of force by the inserter tool (500) during coupling to the adapter (210) actuates the delivery shaft retaining mechanism (310) to release the retained delivery shaft (220) for withdrawal of the delivery shaft assembly (200) from the insert (300) and vial (400), wherein the delivery shaft retaining mechanism (310) comprises a 1st body (312) and 2nd body (314) configured to co-operate to clamp at least a part of the delivery shaft (220), and wherein the 1st body (312) is disposed in fixed relation to the force-receiving body (308), and the 2nd body (314) is configured to at least partly move upon actuation of the delivery shaft retaining mechanism (310) away from the 1st body (312) thereby releasing the retained delivery shaft (220).

2. The package (100) of claim 1, wherein the delivery shaft retaining mechanism (310) further comprises an actuating pin (316) and a movement guide (318), wherein an application of force by the inserter tool during coupling advances the pin (316) and movement guide (318) from a retain position to a release position, wherein the movement guide (318) is slidably coupled to the 2nd body (314) and effects movement of the 2nd body (314) from a retain position to a release position.

3. The package (100) of claim 2, wherein the movement guide (318) comprises at least 1 guiding slot (320) having at least a partly cammed path, the 2nd body (314) comprises at least one protrusion (322) engaged in the guiding slot (320), and movement of the movement guide (318) from the retain to release position effects sliding of the guiding slot (320) and movement of the at least one protrusion (322) along the cammed path thereby separating at least a part of the 2nd body (314) from the 1st body (312).

4. The package (100) of claim 1, wherein the 1st body (312) and the 2nd body (314) are connected by a hinge.

5. The package (100) of claim 4, wherein the hinge is a living hinge.

6. The package (100) of claim 1, wherein the vial holding space (410) is configured for retention of a liquid.

7. The package (100) of claim 1, wherein the vial (400) has an opening (412) which is closable by a cap or removable seal.

8. The package (100) of claim 1, wherein the insert (300) further comprises one or more fluid displacement bodies (340) configured to displace a solution from vial holding space (410) during coupling of the insert (300) into the vial holding space (410).

9. The package (100) of claim 8, whether the insert (300) further comprises an overflow outlet (342) configured for passage of the displaced solution from the vial (400).

10. The package (100) of claim 8, wherein the solution is an aqueous solution.

11. The package (100) of claim 1, wherein the package 100 further comprises the delivery shaft assembly (200).

* * * * *